United States Patent
Schulman et al.

(10) Patent No.: US 11,268,907 B2
(45) Date of Patent: Mar. 8, 2022

(54) DEVICES AND METHODS FOR MINIMIZING FALSE RESULTS FOR TEST SAMPLE REAGENTS ON INSTRUMENT-BASED SYSTEMS

(71) Applicant: Siemens Healthcare Diagnostics Inc., Tarrytown, NY (US)

(72) Inventors: Lloyd Schulman, Granger, IN (US); Christopher Zimmerle, Goshen, IN (US); Julie Chaney, Elkhart, IN (US)

(73) Assignee: Siemens Healthcare Diagnostics Inc., Tarrytown, NY (US)

( * ) Notice: Subject to any disclaimer, the term of this patent is extended or adjusted under 35 U.S.C. 154(b) by 143 days.

(21) Appl. No.: 16/468,532

(22) PCT Filed: Dec. 12, 2017

(86) PCT No.: PCT/US2017/065728
§ 371 (c)(1),
(2) Date: Jun. 11, 2019

(87) PCT Pub. No.: WO2018/111823
PCT Pub. Date: Jun. 21, 2018

(65) Prior Publication Data
US 2020/0072755 A1  Mar. 5, 2020

Related U.S. Application Data

(60) Provisional application No. 62/433,463, filed on Dec. 13, 2016.

(51) Int. Cl.
*G01N 21/78* (2006.01)
*G01N 21/25* (2006.01)
(Continued)

(52) U.S. Cl.
CPC .......... *G01N 21/78* (2013.01); *G01N 21/255* (2013.01); *G01N 21/8483* (2013.01); *G01N 33/52* (2013.01)

(58) Field of Classification Search
CPC .. G01N 21/78; G01N 21/255; G01N 21/8483; G01N 33/52
See application file for complete search history.

(56) References Cited

U.S. PATENT DOCUMENTS 5,055,261 A   10/1991  Khoja et al.
5,408,535 A    4/1995  Howard, III et al.
(Continued)

FOREIGN PATENT DOCUMENTS

EP        2295970 A1    3/2011
JP     2007285988 A    11/2007

OTHER PUBLICATIONS

International Search Report and Written Opinion of International Application No. PCT/US2017/065728 dated Feb. 16, 2018.
(Continued)

*Primary Examiner* — Jennifer Wecker
*Assistant Examiner* — Kathryn Elizabeth Limbaugh
(74) *Attorney, Agent, or Firm* — Dunlap Codding, P.C.

(57) ABSTRACT

Methods of detecting compromise of at least one analyte reagent upon reaction with a test sample are disclosed. Also disclosed are reflectance spectroscopic diagnostic instruments that perform the method, and systems that contain same.

20 Claims, 5 Drawing Sheets
(3 of 5 Drawing Sheet(s) Filed in Color)

(51) Int. Cl.
    *G01N 21/84*     (2006.01)
    *G01N 33/52*     (2006.01)

(56)                   References Cited

U.S. PATENT DOCUMENTS

| | | |
|---|---|---|
| 5,877,863 A | 3/1999 | Ross et al. |
| 2011/0275104 A1 | 11/2011 | Zimmerle et al. |
| 2013/0084630 A1 | 4/2013 | Rolland et al. |
| 2013/0267032 A1 | 10/2013 | Tsai et al. |
| 2016/0069919 A1* | 3/2016 | Holmes .............. G01N 35/0092 506/2 |

OTHER PUBLICATIONS

European Search Report and Search Opinion of European Application No. 17881832.4 dated Dec. 6, 2019.

\* cited by examiner ially used
DEVICES AND METHODS FOR MINIMIZING FALSE RESULTS FOR TEST SAMPLE REAGENTS ON INSTRUMENT-BASED SYSTEMS

CROSS REFERENCE TO RELATED APPLICATIONS/INCORPORATED BY REFERENCE STATEMENT

This application claims priority to U.S. Provisional Application No. 62/433,463, filed Dec. 13, 2016, the disclosure of which is hereby incorporated by reference in its entirety.

BACKGROUND

Sample media such as reagent test strips are widely used in the field of clinical chemistry. A test strip usually has one or more test areas spaced along the length thereof, with each test area being capable of undergoing a color change in response to contact with a liquid specimen. The liquid specimen usually contains one or more analytes or properties of interest. The presence and concentrations of these analytes or properties are determinable by an analysis of the color changes undergone by the test strip. Usually, this analysis involves a color comparison between the test area or test pad and a color standard or scale. In this way, reagent test strips assist physicians in diagnosing the existence of diseases and other health problems or aid in the effectivity of treatments.

Color comparisons made with the naked eye can lead to imprecise measurement. For example, visual color is dependent on the light source present, and when the test strips are read by an individual, the light source may affect the result and lead to errors in conclusions made by the individual. Preferences associated with an individual's perceptions and the potential for a certain level of color blindness can also lead to faulty reporting of results.

Today, strip reading instruments exist that employ reflectance photometry for reading test strip color changes. These instruments, commonly known as photometers, reflectometers, and camera-based instruments (such as, but not limited to, a charge-coupled device (CCD)), are capable of measuring changes resulting from color generating reactions. Since these instruments utilize light sources with known characteristics, the issues encountered when strips are read by the naked eye are overcome. Included among photometers are spectrophotometers, which are capable of responding to more than one range of light wavelengths, e.g., colors. Non-limiting examples of such instruments include those sold under the CLINITEK trademark (e.g., the CLINITEK ADVANTUS®, the CLINITEK ATLAS®, the CLINITEK NOVUS®, and the CLINITEK STATUS®) by Siemens Healthcare Diagnostics Inc. (Tarrytown, N.Y.) and/or as disclosed in U.S. Pat. Nos. 5,055,261; 5,408,535; and 5,877,863 (the entire contents of each of which are fully incorporated by reference herein). These instruments are typically used to detect colors associated with a urine specimen on a MULTISTIX® reagent strip (Siemens Healthcare Diagnostics Inc.), or on relatively large reagent strip rolls or card-based cassettes for high volume automated analysis, such as provided by the CLINITEK® ATLAS® or CLINITEK® NOVUS® Automated Urine Chemistry Analyzers.

BRIEF DESCRIPTION OF THE DRAWINGS

This patent or application file contains at least one drawing executed in color. Copies of this patent or patent application publication with color drawing(s) will be provided by the Office upon request and payment of the necessary fee.

DETAILED DESCRIPTION

Figure 1:
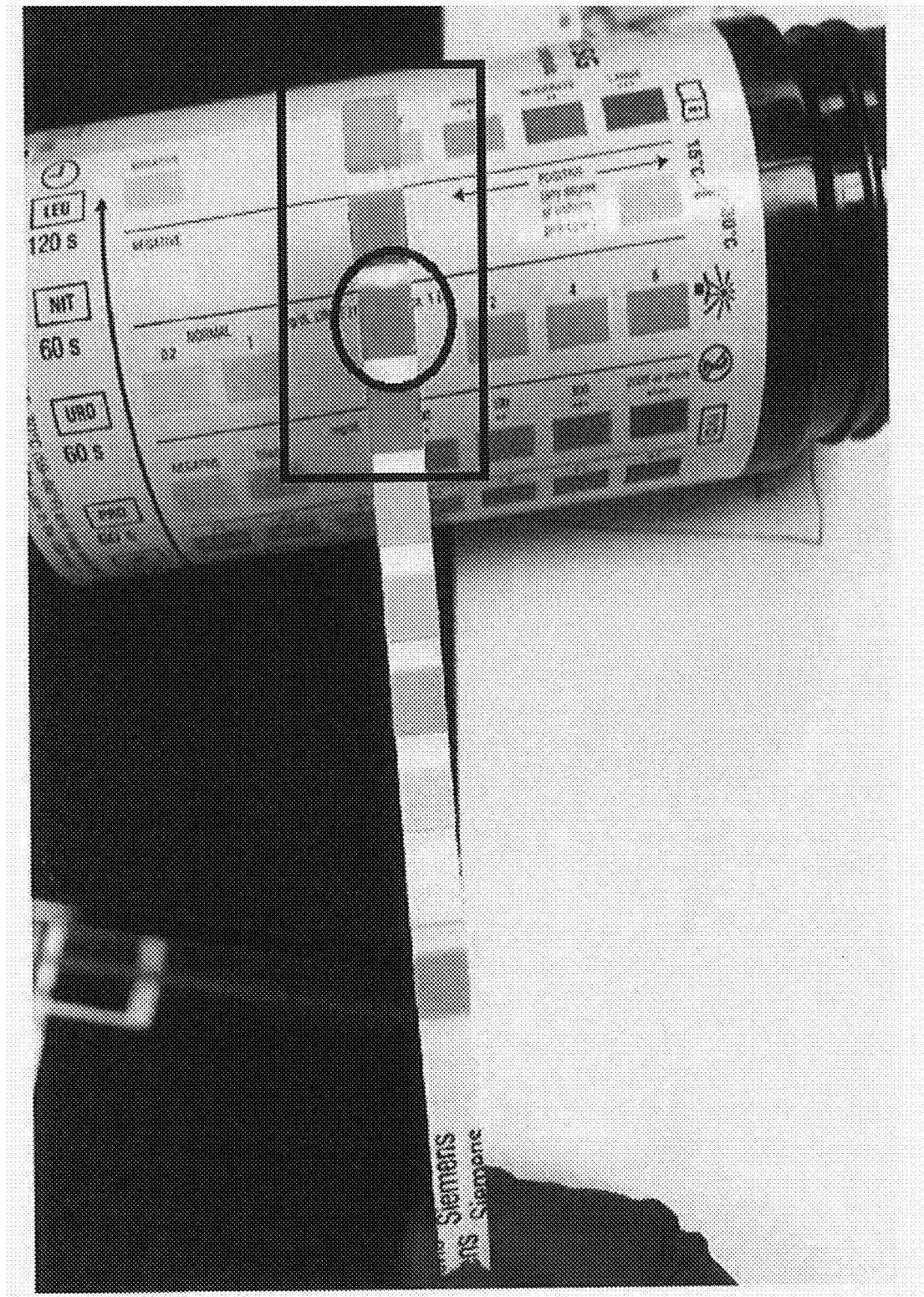
FIG. 1 contains a photograph illustrating a reagent test strip in which multiple analyte reagents have been compromised by reaction with a test sample, whereby the color of each pad on the test strip does not fall within an expected color range for said pad as indicated.

Before explaining at least one embodiment of the inventive concept(s) in detail by way of exemplary language and results, it is to be understood that the inventive concept(s) is not limited in its application to the details of construction and the arrangement of the components set forth in the following description. The inventive concept(s) is capable of other embodiments or of being practiced or carried out in various ways. As such, the language used herein is intended to be given the broadest possible scope and meaning; and the embodiments are meant to be exemplary—not exhaustive. Also, it is to be understood that the phraseology and terminology employed herein is for the purpose of description and should not be regarded as limiting.

Unless otherwise defined herein, scientific and technical terms used in connection with the presently disclosed and/or claimed inventive concept(s) shall have the meanings that are commonly understood by those of ordinary skill in the art. Further, unless otherwise required by context, singular terms shall include pluralities and plural terms shall include the singular. The foregoing techniques and procedures are generally performed according to conventional methods well known in the art and as described in various general and more specific references that are cited and discussed throughout the present specification. The nomenclatures utilized in connection with, and the laboratory procedures and techniques of, analytical chemistry, synthetic organic chemistry, and medicinal and pharmaceutical chemistry described herein are those well-known and commonly used in the art. Standard techniques are used for chemical syntheses and chemical analyses.

All patents, published patent applications, and non-patent publications mentioned in the specification are indicative of the level of skill of those skilled in the art to which this presently disclosed and/or claimed inventive concept(s) pertains. All patents, published patent applications, and non-patent publications referenced in any portion of this application are herein expressly incorporated by reference in their entirety to the same extent as if each individual patent or publication was specifically and individually indicated to be incorporated by reference.

All of the articles, compositions, and/or methods disclosed and/or claimed herein can be made and executed without undue experimentation in light of the present disclosure. While the articles, compositions, and methods of the inventive concept(s) have been described in terms of particular embodiments, it will be apparent to those of skill in the art that variations may be applied to the articles, compositions and/or methods and in the steps or in the sequence of steps of the methods described herein without departing from the concept, spirit and scope of the inventive concept(s). All such similar substitutes and modifications apparent to those skilled in the art are deemed to be within the spirit, scope, and concept of the inventive concept(s) as defined by the appended claims.

As utilized in accordance with the present disclosure, the following terms, unless otherwise indicated, shall be understood to have the following meanings:

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects. The use of the term "at least one" will be understood to include one as well as any quantity more than one, including but not limited to, 2, 3, 4, 5, 10, 15, 20, 30, 40, 50, 100, etc. The term "at least one" may extend up to 100 or 1000 or more, depending on the term to which it is attached; in addition, the quantities of 100/1000 are not to be considered limiting, as higher limits may also produce satisfactory results. In addition, the use of the term "at least one of X, Y, and Z" will be understood to include X alone, Y alone, and Z alone, as well as any combination of X, Y, and Z. The use of ordinal number terminology (i.e., "first," "second," "third," "fourth," etc.) is solely for the purpose of differentiating between two or more items and is not meant to imply any sequence or order or importance to one item over another or any order of addition, for example.

The term "about" is used to indicate that a value includes the inherent variation of error for the device, the method being employed to determine the value and/or the variation that exists among study subjects. For example, but not by way of limitation, when the term "about" is utilized, the designated value may vary by plus or minus twelve percent, or eleven percent, or ten percent, or nine percent, or eight percent, or seven percent, or six percent, or five percent, or four percent, or three percent, or two percent, or one percent.

As used in this specification and claim(s), the words "comprising" (and any form of comprising, such as "comprise" and "comprises"), "having" (and any form of having, such as "have" and "has"), "including" (and any form of including, such as "includes" and "include"), or "containing" (and any form of containing, such as "contains" and "contain") are inclusive or open-ended and do not exclude additional, unrecited elements or method steps.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AAB, BBC, AAABCCCC, CBBAAA, CABABB, and so forth. The skilled artisan will understand that typically there is no limit on the number of items or terms in any combination, unless otherwise apparent from the context.

As used herein, the term "substantially" means that the subsequently described event or circumstance completely occurs or that the subsequently described event or circumstance occurs to a great extent or degree. For example, when associated with a particular event or circumstance, the term "substantially" means that the subsequently described event or circumstance occurs at least 80% of the time, or at least 85% of the time, or at least 90% of the time, or at least 95% of the time. The term "substantially adjacent" may mean that two items are 100% adjacent to one another, or that the two items are within close proximity to one another but not 100% adjacent to one another, or that a portion of one of the two items is not 100% adjacent to the other item but is within close proximity to the other item.

The term "patient" includes human and veterinary subjects. In certain embodiments, a patient is a mammal. In certain other embodiments, the patient is a human. "Mammal" for purposes of treatment refers to any animal classified as a mammal, including human, domestic and farm animals, nonhuman primates, and zoo, sports, or pet animals, such as dogs, horses, cats, cows, etc.

Turning now to particular embodiments, the presently disclosed and/or claimed inventive concept(s) relates generally to improving the performance and reliability of instrument read reagent sample media used to determine the presence of analytes in test samples. In certain non-limiting embodiments, the test sample may be a biological sample such as (but not limited to) urine, and the analytes may include those used to determine the presence of analytes in urine samples, such as (but not limited to) albumin, protein, creatinine, nitrate, nitrite, uristatin, leukocyte esterase (white blood cells), occult blood (red blood cells), ketones, glucose, bilirubin, urobilinogen, hemoglobin, glycosylated hemoglobin, human chorionic gonadotropin, ascorbic acid, pH, specific gravity, and others familiar to those of ordinary skill in the art.

As stated herein above, strip reading instruments exist that employ reflectance photometry for reading test strip color changes, and these instruments are capable of measuring changes resulting from color generating reactions. However, there are occasions where a substance present in the test sample may cause an analyte reagent to turn an unexpected color that is outside of the expected color range. For example, a urine sample may stain the test strip, or a compound present in a urine sample may react in an unexpected manner with one or more analyte reagent(s) present on the strip. Such an unexpected reaction indicates that there is either a problem with the urine sample (for example, a contaminant or an interferent may be located therein) or the urine strip itself. As shown in FIG. 1, this type of compromise of analyte reagents is easily detectable when the color comparison is performed with the naked eye; as can be seen, the colors of at least each of the first four pads on the test strip do not match the expected color range of results for each pad, as indicated on the bottle. For example, the resulting color for the protein (PRO) reagent (i.e., fourth pad down) on the test strip after contact with the biological sample should be a shade of green, as shown on the side of the bottle; however, the PRO test area on the test strip actually turned a shade of orange following contact with the biological sample.

While current strip reading instruments are able to overcome some of the deficiencies seen when strips are read by the naked eye, these instruments typically detect the presence of an analyte based on a change in signal strength at specific wavelength(s) rather than an multi-dimensional color measurement; that is, current strip reading instruments rely on a change in signal strength for a single component of the three dimensional color space to detect the presence of an analyte. Alternatively, certain other strip reading instruments utilize a single, averaged value to represent the color measurement. Since these instruments are limited to an analysis of a single component or averaged value of color, the instruments may not recognize when an analyte reagent is compromised as shown in FIG. 1, and thus said instruments will report a false result in response to this type of interference.

Therefore, there is a need in the art for new and improved devices and methods that identify when reagent analytes are compromised by reaction with a test sample and prevent potentially erroneous results from being reported. It is to such new and improved devices and methods that overcome the defects and disadvantages of the prior art that the presently disclosed and/or claimed inventive concept(s) is directed.

Certain non-limiting embodiments of the presently disclosed and/or claimed inventive concept(s) are directed to methods of detecting compromise of at least one analyte reagent upon reaction with a test sample (such as, but not limited to, a biological sample). In the method, the test sample is reacted with a reagent sample media having at least one test area thereon that contains an analyte reagent configured to react with the test sample and to change color according to an amount of analyte present in the test sample; in certain embodiments, the reagent sample media may have a plurality of said test areas disposed in spaced relation thereon, wherein each of the plurality of test areas contains an analyte reagent configured to react with the test sample and to change color according to an amount of analyte present in the test sample. The reagent sample media is then disposed into a reflectance spectroscopic diagnostic instrument, and a reflectance of light is measured by the instrument across a spectrum of wavelengths for at least one test area using a color model. These reflection measurements are analyzed by the instrument to calculate (quantitatively, semi-quantitatively, or non-quantitatively) at least one factor of color for the at least one test area using a three dimensional color space. The at least one calculated factor of color is compared by the instrument to a known range for all expected positive and negative color results for said test area. The instrument then determines that at least one analyte reagent has been compromised by the test sample if the at least one calculated factor of color for said test area falls outside the known range for that factor.

Any test sample known in the art for use with reagent sample media as described herein may be utilized in accordance with the presently disclosed and/or claimed inventive concept(s). Non-limiting examples of test samples that may be utilized in accordance with the presently disclosed and/or claimed inventive concept(s) include biological samples, pool water samples, aquarium samples, beverage/liquor samples (such as brewery samples and wine samples), and the like.

In certain non-limiting embodiments, the test sample may be a biological sample. Examples of biological samples that may be utilized include, but are not limited to, urine, whole blood or any portion thereof (i.e., plasma or serum), saliva, sputum, cerebrospinal fluid (CSF), intestinal fluid, intraperitoneal fluid, cystic fluid, sweat, interstitial fluid, tears, mucus, bladder wash, semen, fecal, combinations thereof, and the like. In particular non-limiting embodiments, the biological sample is urine.

The term "reagent sample media" refers to any media known in the art as useful for determining the presence of analytes in test samples. For example (but not by way of limitation), the reagent sample media may be based on various liquid assay technologies (such as, but not limited to, urine chemistry technologies). Examples of different formats of reagent sample media include, but are not limited to, reagent test strips, reagent strip rolls, reagent test cards, reagent test cassettes, and the like. Examples of reagent test strips that may be utilized in accordance with the presently disclosed and/or claimed inventive concept(s) include, but are not limited to, reagent test strips such as those produced by Siemens Healthcare Diagnostics Inc. (Tarrytown, N.Y.). Particular non-limiting examples of reagent strips produced by Siemens include the MULTISTIX® family of strips, the CLINITEK® Microalbumin family of strips, and the CLINITEST® hCG family of strips. Particular examples of reagent strip rolls that may be utilized in accordance with the presently disclosed and/or claimed inventive concept(s) include, but are not limited to, the CLINITEK® ATLAS® Reagent Pak (Siemens). Particular examples of card/cassette test formats that may be utilized in accordance with the presently disclosed and/or claimed inventive concept(s) include, but are not limited to, the CLINITEK® NOVUS® test cassettes (Siemens).

Any analytes/analyte reagents that are capable of detection via colorimetric tests and that are capable of use with reagent sample media as described herein may be utilized in accordance with the presently disclosed and/or claimed inventive concept(s). Particular examples of analytes that may be utilized include, but are not limited to, blood, leukocytes, leukocyte esterase, nitrate, nitrite, protein, albumin, creatinine, ketone, bilirubin, urobilinogen, specific gravity, pH, glucose, glycosylated hemoglobin (HbA1C), human chorionic gonadotropin (hCG), albumin-to-creatinine ratio, and protein-to-creatinine ratio.

Any color model known in the art or otherwise contemplated herein that can be utilized by reflectance spectroscopic instruments to produce measurement values that can be analyzed by a three dimensional color space to calculate at least one factor of color falls within the scope of the presently disclosed and/or claimed inventive concept(s). Particular examples of color models that can be utilized include, but are not limited to, RGB (Red Green Blue), YUB (where Y represents luminance and UB represents chrominance), CMY (Cyan Magenta Yellow), CMYK (Cyan Magenta Yellow Key (Black)), and the like.

The analysis of the reflection measurements to calculate (quantitatively, semi-quantitatively, or non-quantitatively) at least one factor of color for the at least one test area can be performed using any three dimensional color space known in the art or otherwise contemplated herein. Particular examples of color spaces that may be utilized include, but are not limited to, HSV (Hue Saturation Value), HSB (Hue Saturation Brightness), HSI (Hue Saturation Intensity), HSL (Hue Saturation Luminance), XYZ, and LAB (where "L" represents lightness and "AB" are color-opponent dimensions), and the like.

In certain non-limiting embodiments, the analysis of the reflection measurements may be used to calculate more than one factor of color for the at least one test area. For example (but not by way of limitation), the measurements may be utilized to calculate at least two factors of color or at least three factors of color. In these embodiments, each of the multiple calculated factors of color is compared by the instrument to a known range for all expected positive and negative color results for said factor of color for said test area. When two or three factors of color are calculated for a single test area, the instrument may determine that at least one analyte reagent has been compromised by the test sample if at least one calculated factor of color for said test area falls outside the known range for that factor; alternatively, the instrument may determine that at least one analyte reagent has been compromised by the test sample if at least two (or all three) calculated factors of color for said test area falls outside the known ranges for said factors/values.

In one non-limiting example, the color space used is HSV, and the at least one factor color that is calculated may be selected from the group comprising hue, saturation, and intensity. That is, in one particular example, the hue value for a test area is compared to known hue value ranges for expected positive and negative color results. In another particular example, the saturation value for a test area is compared to known saturation value ranges for expected positive and negative color results. In yet another particular example, the intensity value for a test area is compared to known intensity value ranges for expected positive and negative color results. In yet a further particular example, the hue and saturation values for a test area are each independently compared to known hue/saturation value ranges for expected positive and negative color results. In yet another particular example, the hue and intensity values for a test area are each independently compared to known hue/intensity value ranges for expected positive and negative color results. In yet a further particular example, the saturation and intensity values for a test area are each independently compared to known saturation/intensity value ranges for expected positive and negative color results.

The measurement, analysis, and determination steps described herein above may be performed by any methods known in the art or otherwise contemplated herein. For example, the reflectance spectroscopic diagnostic instrument may contain a processor that calculates the color of each test area and uses algorithms to perform the comparison and determination steps.

Figure 2:
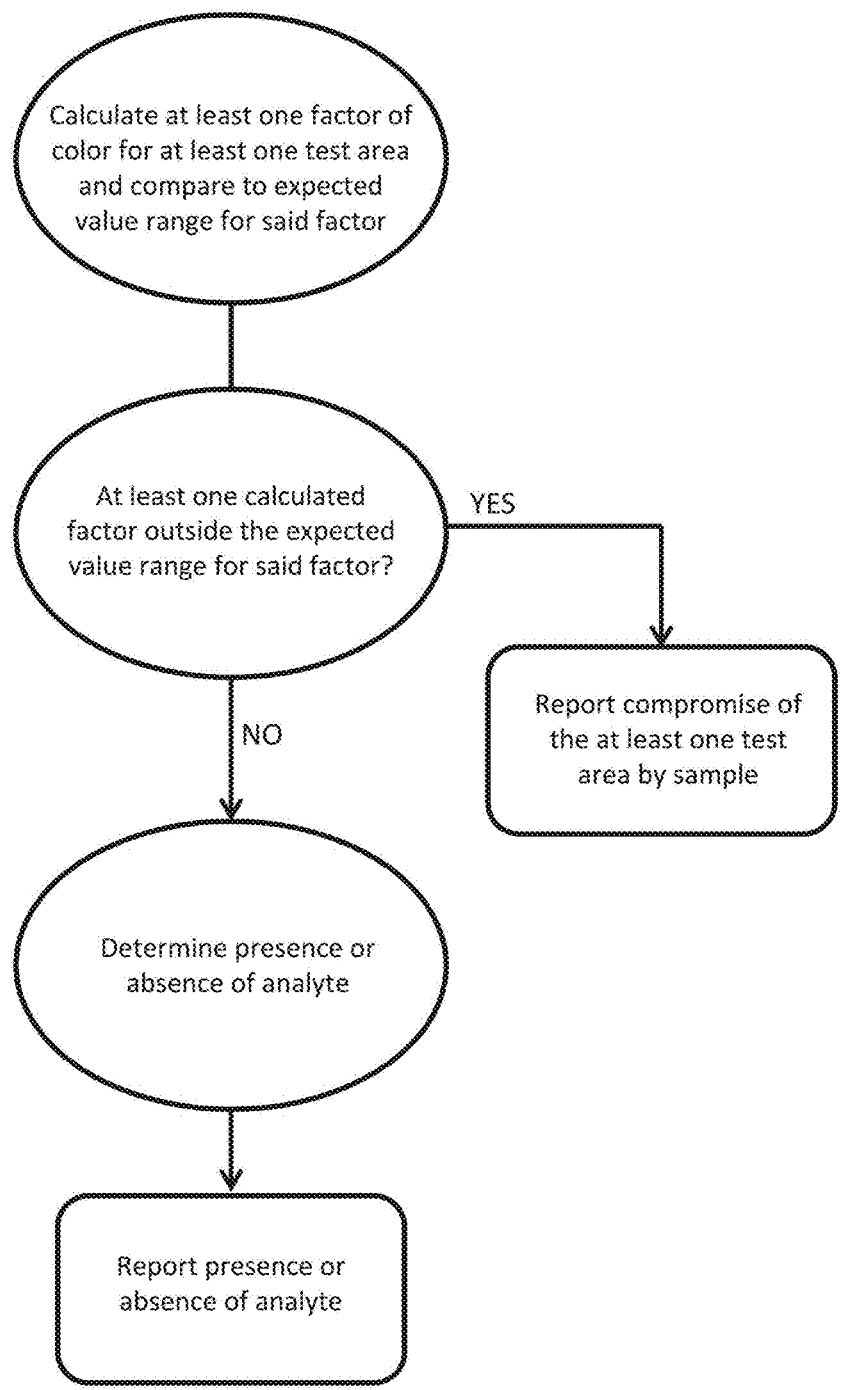
FIG. 2 contains a flow chart for performing one embodiment of the method of the presently disclosed and/or claimed inventive concept(s).

In certain particular embodiments of the method, and as illustrated in FIG. 2, no further results are reported if compromise of one or more test areas is detected and reported. In this embodiment, the method includes reporting that the test sample has compromised the reagent sample media if the value of at least one calculated factor of color falls outside the known value range for said factor for at least one test area. In this embodiment, no further results for the individual test areas of the reagent sample media are reported, and the possibility that the presence of one or more analytes may have been detected will not be reported.

Figure 3:
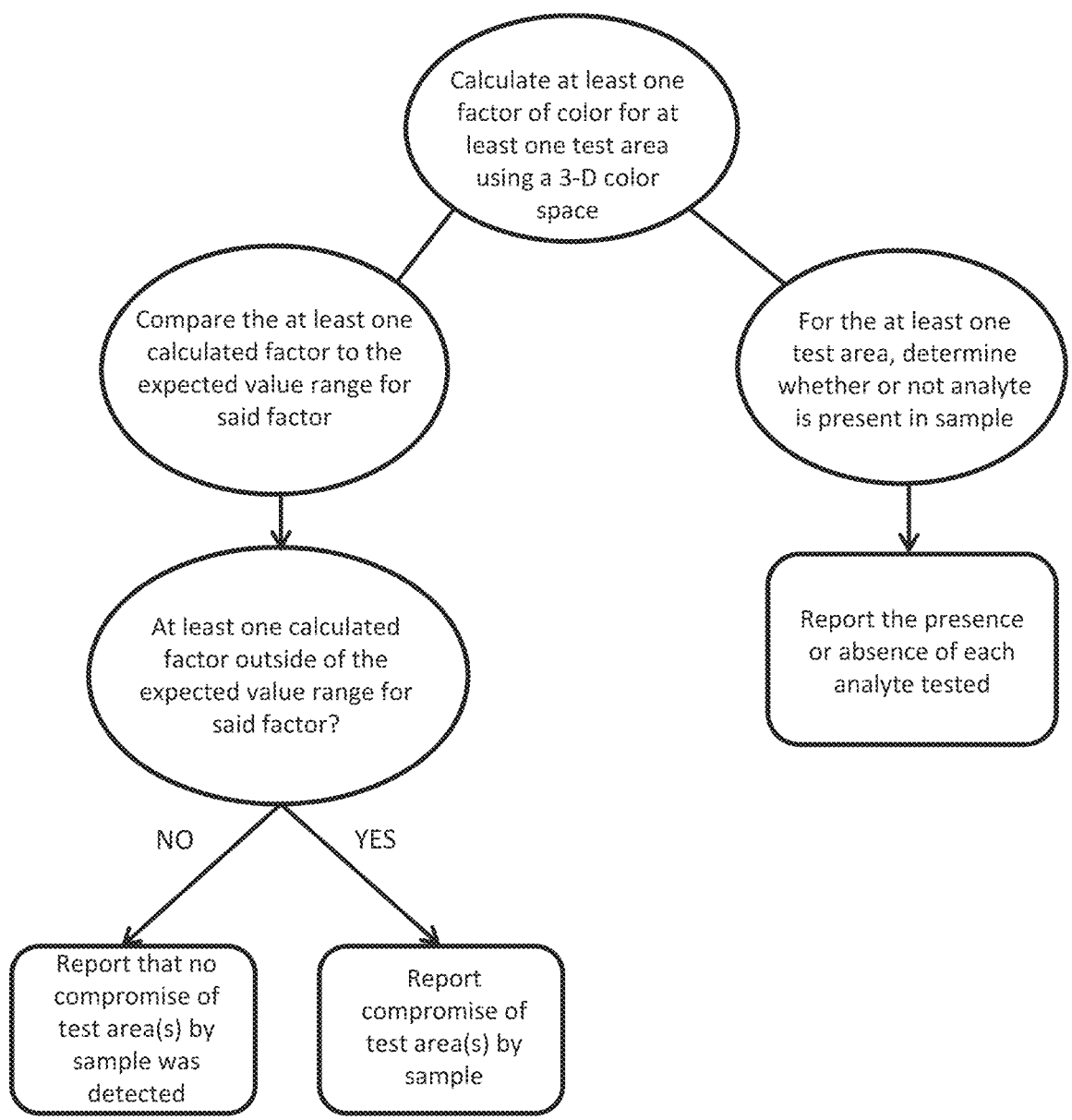
FIG. 3 contains a flow chart for performing another embodiment of the method of the presently disclosed and/or claimed inventive concept(s).

Alternatively, in the particular embodiment illustrated in FIG. 3, the method may include conducting all analyses to determine whether or not at least one analyte is present in the test sample, reporting all results related to the presence or absence of each analyte tested, and then reporting whether or not one or more results may be suspect because at least one test area has been compromised (as detected by the at least one calculated factor of color falling outside the known range for said factor). If no compromise of any of the test area(s) is detected, this result may be directly or indirectly reported; that is, a direct report stating that no compromise was detected may be generated and included with the reporting on the presence or absence of each analyte, or an indirect report of the lack of compromise may be provided simply by the absence of any reporting regarding compromise (i.e., the absence of any report on compromise indicates that no compromise was identified).

The analyses to determine whether or not each of the analytes is present in the test sample may be performed by any methods known in the art or otherwise contemplated herein. For example (but not by way of limitation), any of the methods of detecting the presence of one or more analytes currently utilized with the exemplary instruments and reagent strip/roll/card/cassettes testing formats disclosed in detail herein above may be utilized in accordance with the presently disclosed and/or claimed inventive concept(s). In a particular non-limiting embodiment, a single value may be utilized to determine the presence or absence of an analyte; alternatively, a single, averaged value (such as, but not limited to, an HSV value) may be utilized to determine the presence or absence of an analyte.

Certain embodiments of the presently disclosed and/or claimed inventive concept(s) are directed to a reflectance spectroscopic diagnostic instrument for carrying out any of the methods described or otherwise contemplated herein. The reflectance spectroscopic diagnostic instrument may utilize any of the color models and three dimensional color spaces described herein or otherwise known in the art for utilization with spectroscopic measurements, as described in detail herein above.

In certain non-limiting embodiments, the reflectance spectroscopic diagnostic instrument comprises a holder configured for receiving the reagent sample media therein, at least one light source configured to emit light onto the at least one test area of the reagent sample media, at least one detection device disposed to receive light reflected from the test area(s), and a processor operatively coupled to the detection device and to the light source. The processor configured to analyze reflections received by the at least one detection device and derive at least one factor of color for each test area from the analysis. The at least one factor of color for each test area is then compared to expected positive and negative values for said factor(s). An output corresponding to the above analysis is then generated.

Any light source capable of functioning as part of the reflectance spectroscopic diagnostic instrument and participating in the performance of the methods described or otherwise contemplated herein may be utilized in accordance with the presently disclosed and/or claimed inventive concept(s). Examples of light sources include, but are not limited to, an incandescent lamp, a light emitting diode (LED), and the like.

Any detection device capable of functioning as part of the reflectance spectroscopic diagnostic instrument and participating in the performance of the methods described or otherwise contemplated herein may be utilized in accordance with the presently disclosed and/or claimed inventive concept(s). Examples of light sources include, but are not limited to, a digital camera, and the like.

In certain non-limiting embodiments, the reflectance spectroscopic diagnostic instrument may further include at least one light filter disposed optically between the at least one light source and the test areas of the reagent sample media. In a particular non-limiting embodiment, the light source may be an incandescent lamp, and the reflectance spectroscopic diagnostic instrument may include four filters.

These four filters may include a filter in a wavelength range of about 400 nm to about 510 nm (blue spectrum); a filter in a wavelength range of about 510 nm to about 586 nm (green spectrum); a filter in a wavelength range of about 586 nm to about 660 nm (red spectrum); and a filter in a wavelength range of about 825 nm to about 855 nm (IR spectrum). A particular non-limiting example of a similar hardware configuration can be found in the CLINITEK® ADVANTUS® instrument (Siemens).

In certain other non-limiting embodiments, the at least one light source may be a light emitting diode (LED), and the at least one detection device may be a digital camera. A particular non-limiting example of a similar hardware configuration can be found in the CLINITEK® NOVUS® instrument (Siemens).

In certain other non-limiting embodiments, the at least one light source may include a plurality of LEDs, wherein each LED outputs light at a specific wavelength. For example (but not by way of limitation), the at least one light source may include six LEDs that output at about 470 nm, about 525 nm, about 565 nm, about 625 nm, about 660 nm, and about 845 nm. A particular non-limiting example of a similar hardware configuration can be found in the CLINITEK® STATUS® instrument (Siemens).

Certain additional embodiments of the presently disclosed and/or claimed inventive concept(s) includes a system for detecting compromise of at least one analyte reagent upon reaction with a test sample. The system includes any of the reflectance spectroscopic diagnostic instruments described or otherwise contemplated herein, in combination with reagent sample media having at least one test area containing an analyte reagent configured to react with the test sample and to change color according to an amount of analyte present in the test sample; in certain particular (but non-limiting) embodiments, the reagent sample media has a plurality of said test areas disposed in spaced relation thereon. In the system, the reflectance spectroscopic diagnostic instrument detects if a test sample has compromised at least one of the analyte reagents of the reagent sample media.

Any of the "reacting," "disposing," "measuring," "calculating," "comparing," and/or "determining" steps described herein may be performed, for example but not by way of limitation, by a user. However, as used herein, the term "user" is not limited to use by a human being; rather, the term "user" may comprise (for example, but not by way of limitation) a computer, a server, a website, a processor, a network interface, a human, a user terminal, a virtual computer, combinations thereof, and the like.

The various embodiments of the presently disclosed and/or claimed inventive concept(s) may be utilized with any reflectance spectroscopic diagnostic instrument that is capable of (or has been modified to be capable of) functioning in accordance with the methods described herein. In certain, non-limiting embodiments, the instrument may be a point of care instrument. The reflectance spectroscopic diagnostic instrument may be a system or systems that are able to embody and/or execute the logic of the methods/processes described herein. Logic embodied in the form of software instructions and/or firmware may be executed on any appropriate hardware. For example, logic embodied in the form of software instructions and/or firmware may be executed by one or more components on a dedicated system or systems, on a personal computer system, on a distributed processing computer system, and/or the like. In some embodiments, the entire logic may be implemented in a stand-alone environment operating on an instrument (such as, but not limited to, a point of care instrument). In other embodiments, the logic may be implemented in a networked environment such as a distributed system in which multiple instruments collect data that is transmitted to a centralized computer system for analyzing the data and supplying the results of the analysis to the instruments. Each element of the instrument may be partially or completely network-based or cloud based, and may or may not be located in a single physical location.

Circuitry used herein includes (but is not limited to) analog and/or digital components, or one or more suitably programmed processors (e.g., microprocessors) and associated hardware and software, or hardwired logic. Also, "components" may perform one or more functions. The term "component" may include hardware, such as but not limited to, a processor (e.g., microprocessor), an application specific integrated circuit (ASIC), field programmable gate array (FPGA), a combination of hardware and software, and/or the like.

Software utilized herein may include one or more computer readable medium (i.e., computer readable instructions) that when executed by one or more components cause the component to perform a specified function. It should be understood that the algorithms described herein may be stored on one or more non-transient memory. Non-limiting exemplary non-transient memory may include random access memory, read only memory, flash memory, and/or the like. Such non-transient memory may be electrically based, optically based, and/or the like.

EXAMPLES

Examples are provided hereinbelow. However, the presently disclosed and claimed inventive concept(s) is to be understood to not be limited in its application to the specific experimentation, results and laboratory procedures. Rather, the Examples are simply provided as one of various embodiments and are meant to be exemplary, not exhaustive.

Figure 4:
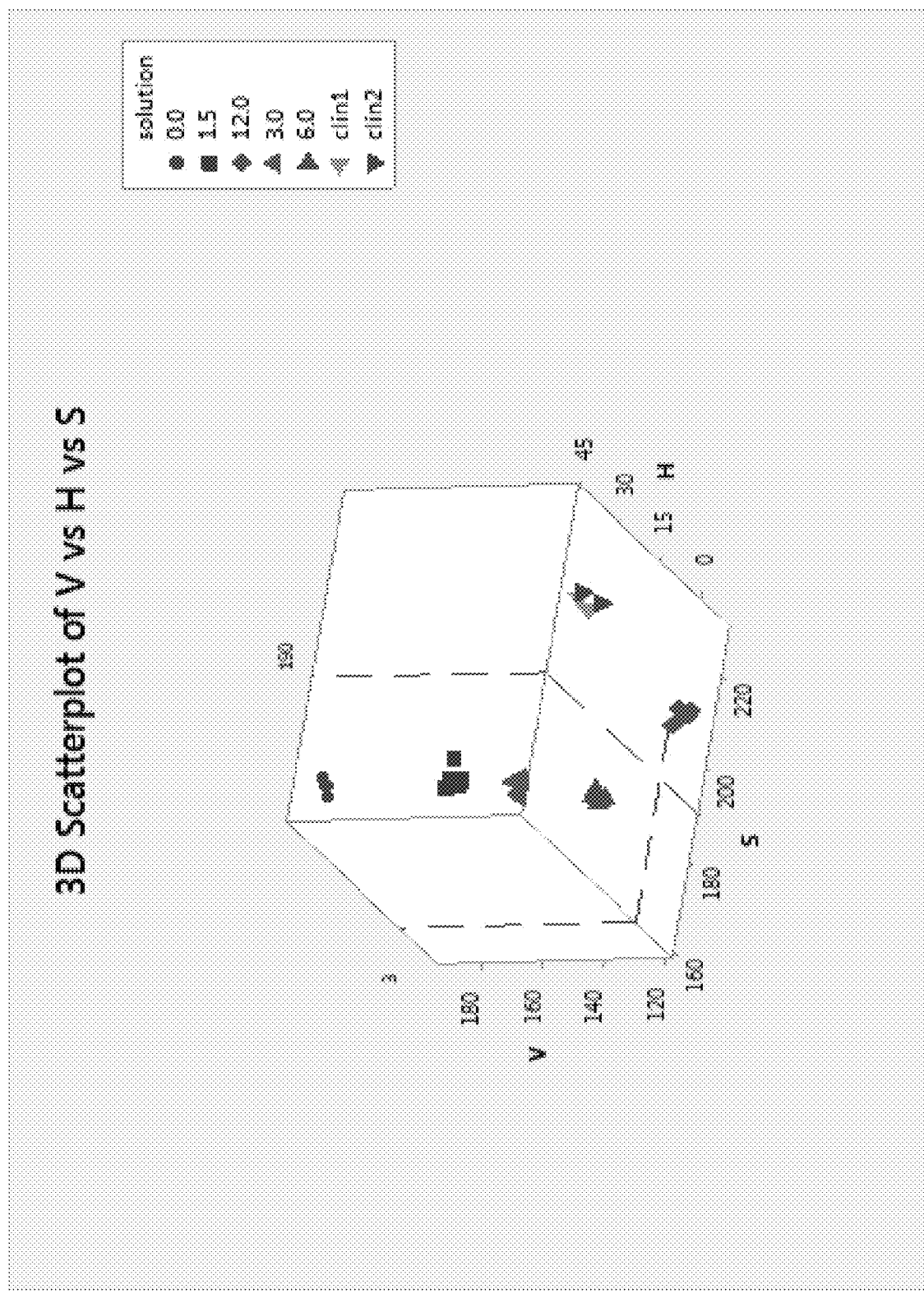
FIG. 4 contains a three-dimensional scatterplot showing HSV data for a urobilinogen (URO) reagent pad on a reagent test strip. Samples include a urobilinogen titration (0.0-12.0 mg/dL) and two clinical samples that generated false positives under the prior art testing methods.
Figure 5:
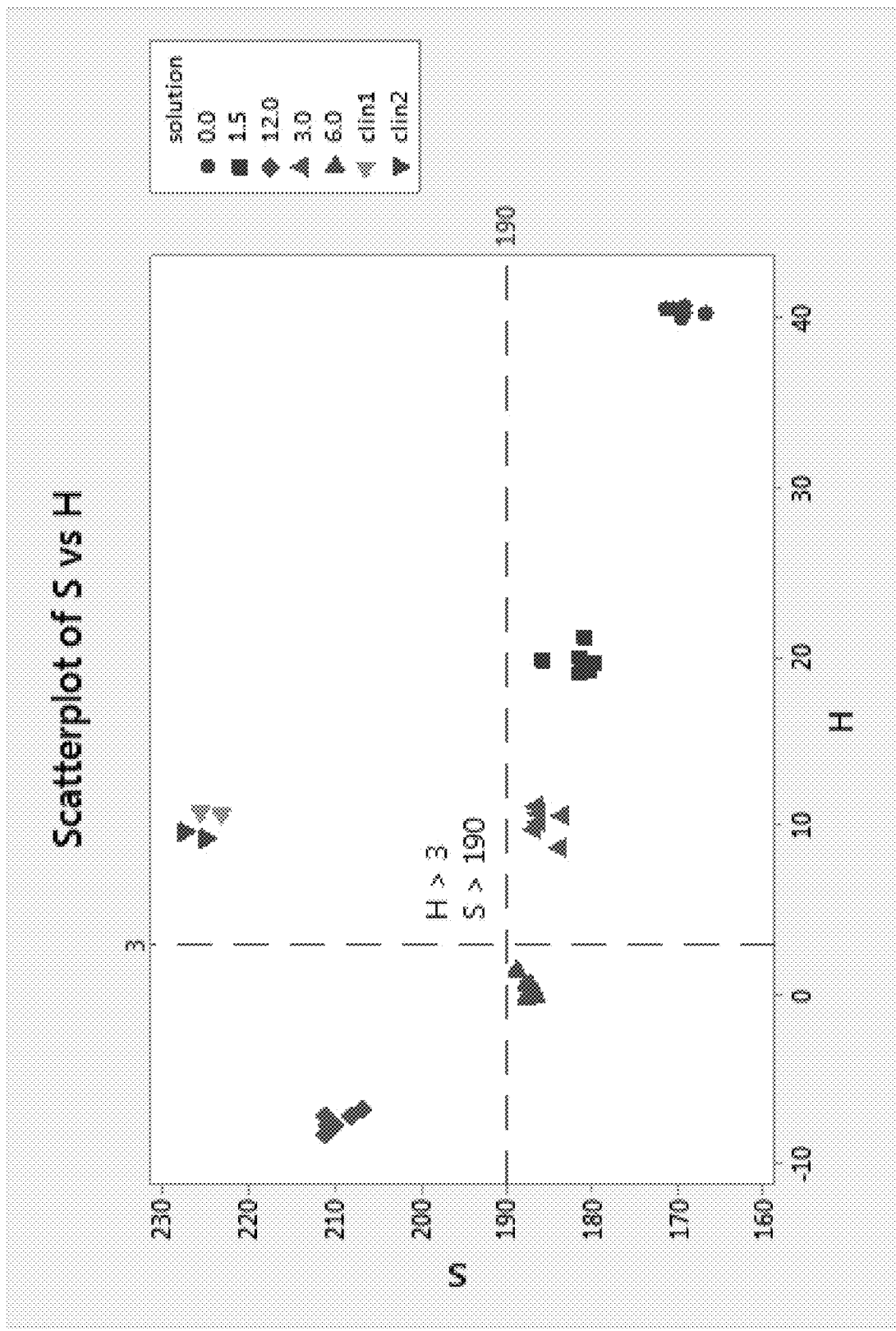
FIG. 5 contains a two-dimensional scatterplot of saturation versus hue values based on the data shown in FIG. 4, along with a non-limiting example of an algorithm developed in accordance with the presently disclosed and/or claimed inventive concept(s) to identify aberrant color results that may generate false positives under the prior art testing methods.

FIG. 4 contains a three-dimensional scatterplot that shows HSV data obtained for a URO reagent pad. Samples included a urobilinogen titration (0.0-12.0 mg/dL) and two clinical samples that generated false positives under the prior art testing methods. The clinical sample results are shown in the black circle and occur in a different region of the color space than the true positive controls, indicating that these samples produced a different color on the reagent pad. The HSV data was then used to develop an algorithm that identified aberrant color results that may generate false positives under the prior art testing methods. For example (but not by way of limitation), one algorithm that was developed based on the data shown in FIG. 4 is indicated on the two-dimensional scatterplot of FIG. 5; as indicated by the dotted line, results that have a Hue (H) value greater than 3 and a Saturation (S) value greater than 190 would be flagged as potential false positives.

Non-Limiting Embodiments of the Inventive Concept(S)

A method of detecting compromise of at least one analyte reagent upon reaction with a test sample by a reflectance spectroscopic diagnostic instrument is provided. The method includes the steps of: (a) measuring a reflectance of light across a spectrum of wavelengths for at least one test area on a reagent sample media that has been reacted with a test sample, the reagent sample media having at least one test area disposed thereon, wherein the at least one test area contains an analyte reagent configured to react with the test sample and to change color according to an amount of analyte present in the test sample, wherein the measurements are performed by a reflectance spectroscopic diagnostic instrument in which the reagent sample media has been disposed, and wherein the measurements use a color model; (b) analyzing the measurements obtained in (a) to calculate at least one factor of color for the at least one test area using a three dimensional color space; (c) comparing the at least one calculated factor of color for the at least one test area to known ranges of expected color results for the at least one test area; and (d) determining that at least one analyte reagent has been compromised by the test sample if the at least one calculated factor of color for the at least one test area falls outside the known range for said factor. Each of steps (a)-(d) may be performed by the reflectance spectroscopic diagnostic instrument.

In one non-limiting embodiment, the method further includes the step of: (e) reporting that the test sample has compromised at least one test area on the reagent sample media if the at least one calculated factor of color falls outside the known range for said factor of color for the at least one test area. In this embodiment, no further results for the at least one test area of the reagent sample media may be reported.

In another alternative non-limiting embodiment, the method may further include the steps of: (d) determining whether or not at least one analyte is present in the test sample; (h) reporting the presence or absence of each analyte tested; and (i) reporting that the at least one test area has been compromised if the at least one calculated factor of color falls outside a known value range for said factor of color.

In the above methods, the test sample may be a biological sample. In certain non-limiting embodiments, the biological sample may be selected from the group comprising urine, whole blood or any portion thereof, saliva, sputum, cerebrospinal fluid, intestinal fluid, intraperitoneal fluid, cystic fluid, sweat, interstitial fluid, tears, mucus, bladder wash, semen, fecal, and combinations thereof. In a particular non-limiting embodiment, the biological sample is urine. In addition, when the test sample is a biological sample (such as, but not limited to, urine), each of the analytes may be selected from the group comprising at least one of blood, leukocytes, leukocyte esterase, nitrate, nitrite, protein, albumin, creatinine, ketone, bilirubin, urobilinogen, specific gravity, pH, glucose, glycosylated hemoglobin (HbA1C), human chorionic gonadotropin (hCG), albumin-to-creatinine ratio, ascorbic acid, and protein-to-creatinine ratio.

In certain non-limiting embodiments, the color model used in step (a) may be selected from the group comprising RGB, YUB, CMY, and CMYK, while the three dimensional color space used in step (b) may be selected from the group comprising HSV, HSB, HSI, HSL, XYZ, and LAB.

In certain non-limiting embodiments, the reagent sample media may have a plurality of test areas disposed in spaced relation thereon. In this embodiment, steps (b)-(d) above may be performed for each of the plurality of test areas.

In certain non-limiting embodiments, steps (b)-(d) of the method are further defined as: (b) analyzing the measurements obtained in (a) to calculate at least two factors of color for the at least one test area using a three dimensional color space; (c) comparing each of the at least two calculated factors of color for the at least one test area to a known range of expected color results for the at least one test area; and (d) determining that at least one analyte reagent has been compromised by the test sample if at least one of the at least two calculated factors of color for a test area falls outside the known range for said factor. In these embodiments, step (d) may also be further defined as determining that at least one analyte reagent has been compromised by the test sample if both of the at least two calculated factors of color for a test area fall outside the known ranges for said factors.

In certain non-limiting embodiments, steps (b)-(d) of the method are further defined as: (b) analyzing the measurements obtained in (a) to calculate at least three factors of color for the at least one test area using a three dimensional color space; (c) comparing each of the at least three calculated factors of color for the at least one test area to a known range of expected color results for the at least one test area; and (d) determining that at least one analyte reagent has been compromised by the test sample if at least one of the at least three calculated factors of color for a test area falls outside the known range for said factor. In said embodiments, step (d) may alternatively be further defined as determining that at least one analyte reagent has been compromised by the test sample if at least two of the at least three calculated factors of color for a test area fall outside the known ranges for said factors. In yet another alternative, step (d) may be further defined as determining that at least one analyte reagent has been compromised by the test sample if all of the at least three calculated factors of color for a test area fall outside the known ranges for said factors.

Also provided is a reflectance spectroscopic diagnostic instrument for carrying out any of the above methods. In certain non-limiting embodiments, the reflectance spectroscopic diagnostic instrument uses a color model selected from the group comprising RGB, YUB, CMY, and CMYK, and a three dimensional color space selected from the group comprising HSV, HSB, HSI, HSL, XYZ, and LAB.

In certain non-limiting embodiments, the reflectance spectroscopic diagnostic instrument further includes: a holder configured for receiving the reagent sample media therein; at least one light source configured to emit light onto the at least one test area of the reagent sample media; at least one detection device disposed to receive light reflected from the at least one test area; and a processor operatively coupled to the detection device and to the light source. The processor is configured to: analyze reflections received by the at least one detection device; derive at least one factor of color for the at least one test area from the analysis; compare the at least one factor of color for each test area to known ranges of expected values for said factor; and generate an output corresponding thereto.

In certain non-limiting embodiments, the reflectance spectroscopic diagnostic instrument further includes at least one light filter disposed optically between the at least one light source and the at least one test area of the reagent sample media. In certain particular non-limiting embodiments, the at least one light source is an incandescent lamp, and wherein the at least one light filter is further defined as comprising: a filter in a wavelength range of about 400 nm to about 510 nm; a filter in a wavelength range of about 510 nm to about 586 nm; a filter in a wavelength range of about 586 nm to about 660 nm; and a filter in a wavelength range of about 825 nm to about 855 nm.

In certain non-limiting embodiments, the at least one light source may be a light emitting diode (LED). In a particular non-limiting embodiment, the at least one light source may be a light emitting diode (LED), and the at least one detection device is a digital camera. Alternatively, the at least one light source may include a plurality of LEDs, wherein each LED outputs light at a specific wavelength. For example (but not by way of limitation), the reflectance spectroscopic diagnostic instrument may include six LEDs that output at about 470 nm, about 525 nm, about 565 nm, about 625 nm, about 660 nm, and about 845 nm.

Also provided is a system for detecting compromise of at least one analyte reagent upon reaction with a test sample. The system includes any of the reflectance spectroscopic diagnostic instruments described herein above in combination with reagent sample media having at least one test area disposed thereon. The at least one test area contains an analyte reagent configured to react with the test sample and to change color according to an amount of analyte present in the test sample. The reflectance spectroscopic diagnostic instrument detects if a test sample has compromised at least one of the analyte reagents.

In certain embodiments, the analytes are selected from the group comprising at least one of blood, leukocytes, leukocyte esterase, nitrate, nitrite, protein, albumin, creatinine, ketone, bilirubin, urobilinogen, specific gravity, pH, glucose, glycosylated hemoglobin (HbA1C), human chorionic gonadotropin (hCG), ascorbic acid, albumin-to-creatinine ratio, and protein-to-creatinine ratio.

In certain embodiments, the reagent sample media has a plurality of test areas disposed in spaced relation thereon.

Thus, in accordance with the presently disclosed and/or claimed inventive concept(s), there have been provided compositions, kits, devices, and instruments, as well as methods of producing and using same, which fully satisfy the objectives and advantages set forth hereinabove. Although the inventive concept(s) has been described in conjunction with the specific language set forth hereinabove, it is evident that many alternatives, modifications, and variations will be apparent to those skilled in the art. Accordingly, it is intended to embrace all such alternatives, modifications, and variations that fall within the spirit and broad scope of the presently disclosed and/or claimed inventive concept(s).

The following is a list of non-limiting illustrative embodiments of the inventive concepts disclosed herein:

1. A method of detecting compromise of at least one analyte reagent upon reaction with a test sample by a reflectance spectroscopic diagnostic instrument, the method comprising the steps of:

(a) measuring a reflectance of light across a spectrum of wavelengths for at least one test area on a reagent sample media that has been reacted with a test sample, the reagent sample media having at least one test area disposed thereon, wherein the at least one test area contains an analyte reagent configured to react with the test sample and to change color according to an amount of analyte present in the test sample, and wherein the measurements are performed by a reflectance spectroscopic diagnostic instrument in which the reagent sample media has been disposed and using a color model;

(b) analyzing the measurements obtained in (a) to calculate at least one factor of color for the at least one test area using a three dimensional color space;

(c) comparing the at least one calculated factor of color for the at least one test area to a known range of expected color results for the at least one test area; and (d) determining that at least one analyte reagent has been compromised by the test sample if the at least one calculated factor of color for the at least one test area falls outside the known range for said factor; and wherein steps (a)-(d) are performed by the reflectance spectroscopic diagnostic instrument.

2. The illustrative method of embodiment 1, further comprising the step of:

(e) reporting that the test sample has compromised at least one test area on the reagent sample media if the at least one calculated factor of color falls outside the known range for said factor of color for the at least one test area.

3. The illustrative method of embodiment 2, wherein no further results for the at least one test area of the reagent sample media is reported.

4. The illustrative method of embodiment 1, wherein the method further comprises the steps of:

(e) determining whether or not the at least one analyte is present in the test sample;

(f) reporting the presence or absence of each analyte tested; and (g) reporting that the at least one test area has been compromised if the at least one calculated factor of color falls outside a known value range for said factor of color.

5. The illustrative method of any of embodiments 1-4, wherein the test sample is a biological sample selected from the group comprising urine, whole blood or any portion thereof, saliva, sputum, cerebrospinal fluid, intestinal fluid, intraperitoneal fluid, cystic fluid, sweat, interstitial fluid, tears, mucus, bladder wash, semen, fecal, and combinations thereof.

6. The illustrative method of embodiment 5, wherein the biological sample is urine.

7. The illustrative method of embodiment 5 or 6, wherein each of the analytes is selected from the group comprising at least one of blood, leukocytes, leukocyte esterase, nitrate, nitrite, protein, albumin, creatinine, ketone, bilirubin, urobilinogen, specific gravity, pH, glucose, glycosylated hemoglobin (HbA1C), human chorionic gonadotropin (hCG), albumin-to-creatinine ratio, ascorbic acid, and protein-to-creatinine ratio.

8. The illustrative method of any of embodiments 1-7, wherein the reagent sample media has a plurality of test areas disposed in spaced relation thereon.

9. The illustrative method of embodiment 8, wherein steps (b)-(d) are performed for each of the plurality of test areas.

10. The illustrative method of any of embodiments 1-9, wherein the color model used in step (a) is selected from the group comprising RGB, YUB, CMY, and CMYK.

11. The illustrative method of any of embodiments 1-10, wherein the three dimensional color space used in step (b) is selected from the group comprising HSV, HSB, HSI, HSL, XYZ, and LAB.

12. The illustrative method of any of embodiments 1-11, wherein steps (b)-(d) are further defined as:

(b) analyzing the measurements obtained in (a) to calculate at least two factors of color for the at least one test area using a three dimensional color space;

(c) comparing each of the at least two calculated factors of color for the at least one test area to a known range of expected color results for the at least one test area; and (d) determining that at least one analyte reagent has been compromised by the test sample if at least one of the at least two calculated factors of color for a test area falls outside the known range for said factor.

13. The illustrative method of embodiment 12, wherein step (d) is further defined as:

(d) determining that at least one analyte reagent has been compromised by the test sample if both of the at least two calculated factors of color for a test area fall outside the known ranges for said factors.

14. The illustrative method of any of embodiments 1-11, wherein steps (b)-(d) are further defined as:

(b) analyzing the measurements obtained in (a) to calculate at least three factors of color for the at least one test area using a three dimensional color space;

(c) comparing each of the at least three calculated factors of color for the at least one test area to a known range of expected color results for the at least one test area; and (d) determining that at least one analyte reagent has been compromised by the test sample if at least one of the at least three calculated factors of color for a test area falls outside the known range for said factor.

15. The illustrative method of embodiment 14, wherein step (d) is further defined as:

(d) determining that at least one analyte reagent has been compromised by the test sample if at least two of the at least three calculated factors of color for a test area fall outside the known ranges for said factors.

16. The illustrative method of embodiment 15, wherein step (d) is further defined as:

(d) determining that at least one analyte reagent has been compromised by the test sample if all of the at least three calculated factors of color for a test area fall outside the known ranges for said factors.

17. A illustrative reflectance spectroscopic diagnostic instrument for carrying out the method of any of embodiments 1-16.

18. The illustrative reflectance spectroscopic diagnostic instrument of embodiment 17, wherein the reflectance spectroscopic diagnostic instrument uses a color model selected from the group comprising RGB, YUB, CMY, and CMYK, and a three dimensional color space selected from the group comprising HSV, HSB, HSI, HSL, XYZ, and LAB.

19. The illustrative reflectance spectroscopic diagnostic instrument of embodiment 17 or 18, further comprising:

a holder configured for receiving the reagent sample media therein;

at least one light source configured to emit light onto the at least one test area of the reagent sample media;

at least one detection device disposed to receive light reflected from the at least one test area;

a processor operatively coupled to the detection device and to the light source, the processor configured to:

analyze reflections received by the at least one detection device;

derive at least one factor of color for the at least one test area from the analysis;

compare the at least one factor of color for the at least one test area to known ranges of expected results for the at least one factor; and generate an output corresponding thereto.

20. The illustrative reflectance spectroscopic diagnostic instrument of embodiment 19, further comprising at least one light filter disposed optically between the at least one light source and the at least one test area of the reagent sample media.

21. The illustrative reflectance spectroscopic diagnostic instrument of embodiment 20, wherein the at least one light source is an incandescent lamp, and wherein the at least one light filter is further defined as comprising:

a filter in a wavelength range of about 400 nm to about 510 nm;

a filter in a wavelength range of about 510 nm to about 586 nm;

a filter in a wavelength range of about 586 nm to about 660 nm; and a filter in a wavelength range of about 825 nm to about 855 nm.

22. The illustrative reflectance spectroscopic diagnostic instrument of embodiment 19, wherein the at least one light source is a light emitting diode (LED).

23. The illustrative reflectance spectroscopic diagnostic instrument of embodiment 22, wherein the at least one detection device is a digital camera.

24. The illustrative reflectance spectroscopic diagnostic instrument of embodiment 22, wherein the at least one light source comprises a plurality of LEDs, wherein each LED outputs light at a specific wavelength.

25. The illustrative reflectance spectroscopic diagnostic instrument of embodiment 24, comprises six LEDs that output at about 470 nm, about 525 nm, about 565 nm, about 625 nm, about 660 nm, and about 845 nm.

26. An illustrative system for detecting compromise of at least one analyte reagent upon reaction with a test sample, the system comprising:

the reflectance spectroscopic diagnostic instrument of any of embodiments 17-25; and reagent sample media having at least one test area disposed thereon, wherein the at least one test area contains an analyte reagent configured to react with the test sample and to change color according to an amount of analyte present in the test sample; and wherein the reflectance spectroscopic diagnostic instrument detects if a test sample has compromised at least one of the analyte reagents.

27. The illustrative system of embodiment 26, wherein each of the analytes is selected from the group comprising at least one of blood, leukocytes, leukocyte esterase, nitrate, nitrite, protein, albumin, creatinine, ketone, bilirubin, urobilinogen, specific gravity, pH, glucose, glycosylated hemoglobin (HbA1C), human chorionic gonadotropin (hCG), ascorbic acid, albumin-to-creatinine ratio, and protein-to-creatinine ratio.

28. The illustrative system of embodiment 26 or 27, wherein the reagent sample media has a plurality of test areas disposed in spaced relation thereon.

What is claimed is:

1. A method of detecting compromise of at least one analyte reagent upon reaction with a test sample by a reflectance spectroscopic diagnostic instrument, the method comprising the steps of:

(a) measuring a reflectance of light across a spectrum of wavelengths for at least one test area on a reagent sample media that has been reacted with a test sample, the reagent sample media having at least one test area disposed thereon, wherein the at least one test area contains an analyte reagent configured to react with the test sample and to change color according to an amount of analyte present in the test sample, and wherein the measurements are performed by a reflectance spectroscopic diagnostic instrument in which the reagent sample media has been disposed and using a color model;

(b) analyzing the measurements obtained in (a) to calculate at least three factors of color for the at least one test area using a three dimensional color space;

(c) independently comparing each of the at least three calculated factors of color for the at least one test area to a known range of all expected positive and negative color results for the at least one test area, wherein the known range of expected color results are stored as an algorithm in a memory accessible by circuitry of the reflectance spectroscopic diagnostic instrument; and (d) determining that at least one analyte reagent has been compromised by the test sample if at least one calculated factor of the at least three calculated factors of color for the at least one test area falls outside the known range for said factor; and wherein steps (a)-(d) are performed by the reflectance spectroscopic diagnostic instrument.

2. The method of claim 1, further comprising the step of:
(e) reporting that the test sample has compromised at least one test area on the reagent sample media if at least one calculated factor of the at least three calculated factors of color falls outside the known range for said factor of color for the at least one test area.

3. The method of claim 1, wherein the method further comprises the steps of:
(e) determining whether or not the at least one analyte is present in the test sample;
(f) reporting the presence or absence of each analyte tested; and
(g) reporting that the at least one test area has been compromised if at least one calculated factor of the at least three calculated factors of color falls outside a known value range for said factor of color.

4. The method of claim 1, wherein the reagent sample media has a plurality of test areas disposed in spaced relation thereon.

5. The method of claim 4, wherein steps (b)-(d) are performed for each of the plurality of test areas.

6. The method of claim 1, wherein the color model used in step (a) is selected from the group consisting of RGB, YUB, CMY, and CMYK.

7. The method of claim 1, wherein the three dimensional color space used in step (b) is selected from the group consisting of HSV, HSB, HSI, HSL, XYZ, and LAB.

8. The method of claim 1, wherein step (d) is further defined as:
(d) determining that at least one analyte reagent has been compromised by the test sample if at least two of the at least three calculated factors of color for a test area fall outside the known ranges for said factors.

9. The method of claim 8, wherein step (d) is further defined as:
(d) determining that at least one analyte reagent has been compromised by the test sample if all of the at least three calculated factors of color for a test area fall outside the known ranges for said factors.

10. A reflectance spectroscopic diagnostic instrument for carrying out the method of claim 1, wherein the reflectance spectroscopic diagnostic instrument comprises a memory that is accessible by circuitry, and wherein the known range of expected color results are stored in the memory.

11. The reflectance spectroscopic diagnostic instrument of claim 10, further comprising: a holder configured for receiving the reagent sample media therein; at least one light source configured to emit light onto the at least one test area of the reagent sample media; at least one detection device disposed to receive light reflected from the at least one test area; a processor operatively coupled to the detection device and to the light source, the processor programmed to: analyze reflections received by the at least one detection device; derive at least three factors of color for the at least one test area from the analysis; compare the at least three factors of color for the at least one test area to known ranges of expected results for the at least three factors; and generate an output corresponding thereto.

12. The reflectance spectroscopic diagnostic instrument of claim 11, further comprising at least one light filter disposed optically between the at least one light source and the at least one test area of the reagent sample media.

13. The reflectance spectroscopic diagnostic instrument of claim 12, wherein the at least one light source is an incandescent lamp, and wherein the at least one light filter is further defined as comprising:
a filter in a wavelength range of about 400 nm to about 510 nm;
a filter in a wavelength range of about 510 nm to about 586 nm;
a filter in a wavelength range of about 586 nm to about 660 nm; and
a filter in a wavelength range of about 825 nm to about 855 nm.

14. The reflectance spectroscopic diagnostic instrument of claim 11, wherein the at least one light source is a light emitting diode (LED).

15. The reflectance spectroscopic diagnostic instrument of claim 14, wherein the at least one light source comprises a plurality of LEDs, wherein each LED outputs light at a specific wavelength.

16. The reflectance spectroscopic diagnostic instrument of claim 15, comprises six LEDs that output at about 470 nm, about 525 nm, about 565 nm, about 625 nm, about 660 nm, and about 845 nm.

17. A system for detecting compromise of at least one analyte reagent upon reaction with a test sample, the system comprising:
the reflectance spectroscopic diagnostic instrument of claim 10; and
reagent sample media having a plurality of test areas disposed thereon, wherein each of the test areas contains an analyte reagent configured to react with the test sample and to change color according to an amount of analyte present in the test sample; and
wherein the reflectance spectroscopic diagnostic instrument detects if a test sample has compromised at least one of the analyte reagents.

18. The method of claim 1, wherein the test sample is a biological sample selected from the group consisting of urine, whole blood or any portion thereof, saliva, sputum, cerebrospinal fluid, intestinal fluid, intraperitoneal fluid, cystic fluid, sweat, interstitial fluid, tears, mucus, bladder wash, semen, fecal, and combinations thereof.

19. The method of claim 18, wherein the test sample is urine.

20. The method of claim 3, wherein the at least one analyte in steps (e)-(f) is selected from the group consisting of blood, leukocytes, leukocyte esterase, nitrate, nitrite, protein, albumin, creatinine, ketone, bilirubin, urobilinogen, specific gravity, pH, glucose, glycosylated hemoglobin (HbA1C), human chorionic gonadotropin (hCG), albumin-to-creatinine ratio, ascorbic acid, and protein-to-creatinine ratio.

* * * * *